United States Patent [19]

Halbert et al.

[11] Patent Number: 4,954,645
[45] Date of Patent: Sep. 4, 1990

[54] DITHIOACID RHENIUM SULFIDE DIMER COMPOSITIONS

[75] Inventors: Thomas R. Halbert, Annandale; Liwen Wei, Somerville; Edward I. Stiefel, Bridgewater, all of N.J.

[73] Assignee: Exxon Research and Engineering Company, Florham Park, N.J.

[21] Appl. No.: 385,049

[22] Filed: Jul. 26, 1989

Related U.S. Application Data

[63] Continuation of Ser. No. 202,341, Jun. 6, 1988, abandoned.

[51] Int. Cl.$^5$ .............................................. C07F 13/00
[52] U.S. Cl. ........................................ 556/45; 556/49
[58] Field of Search ................................... 556/49, 45

[56] References Cited

PUBLICATIONS

Rowbottom et al., "J. Chem. Soc. Dalton", 1974, pp. 684–689.
Rowbottom et al., "J. Chem. Soc. Dalton", 1972, pp. 826–830.
Belousov et al., "Reset. Kinet. Catal. Lett.", 21(3), pp. 371–375 (1982).
Fletcher et al., "J. Chem. Soc. Dalton", 1974, pp. 486–489.
Griffith, "J. Chem. Soc. A," 2, pp. 211–218 (1969).
Nitra et al., "Z. Anoy. Ally. Chem.", 548 (1982), pp. 217–224.

*Primary Examiner*—Paul F. Shaver
*Attorney, Agent, or Firm*—Joseph J. Dvorak

[57] ABSTRACT

Briefly stated, the present invention encompasses a new class of rhenium 1,1-dithioacid complexes and their method of preparation. The complexes have the general formula $[L_2Re(\mu\text{-}S)]_2$ wherein L is a dithioacid or similar ligand, and $\mu$ denotes the fact that the sulfur atoms in the core of the complex bridge the two rhenium atoms in the complex. Thus, the core structure for such typical compounds is generally of the form:

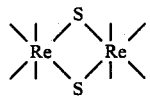

where the dangling valences are associated with the sulfur atoms of a 1,1-dithioacid, L.

8 Claims, 1 Drawing Sheet

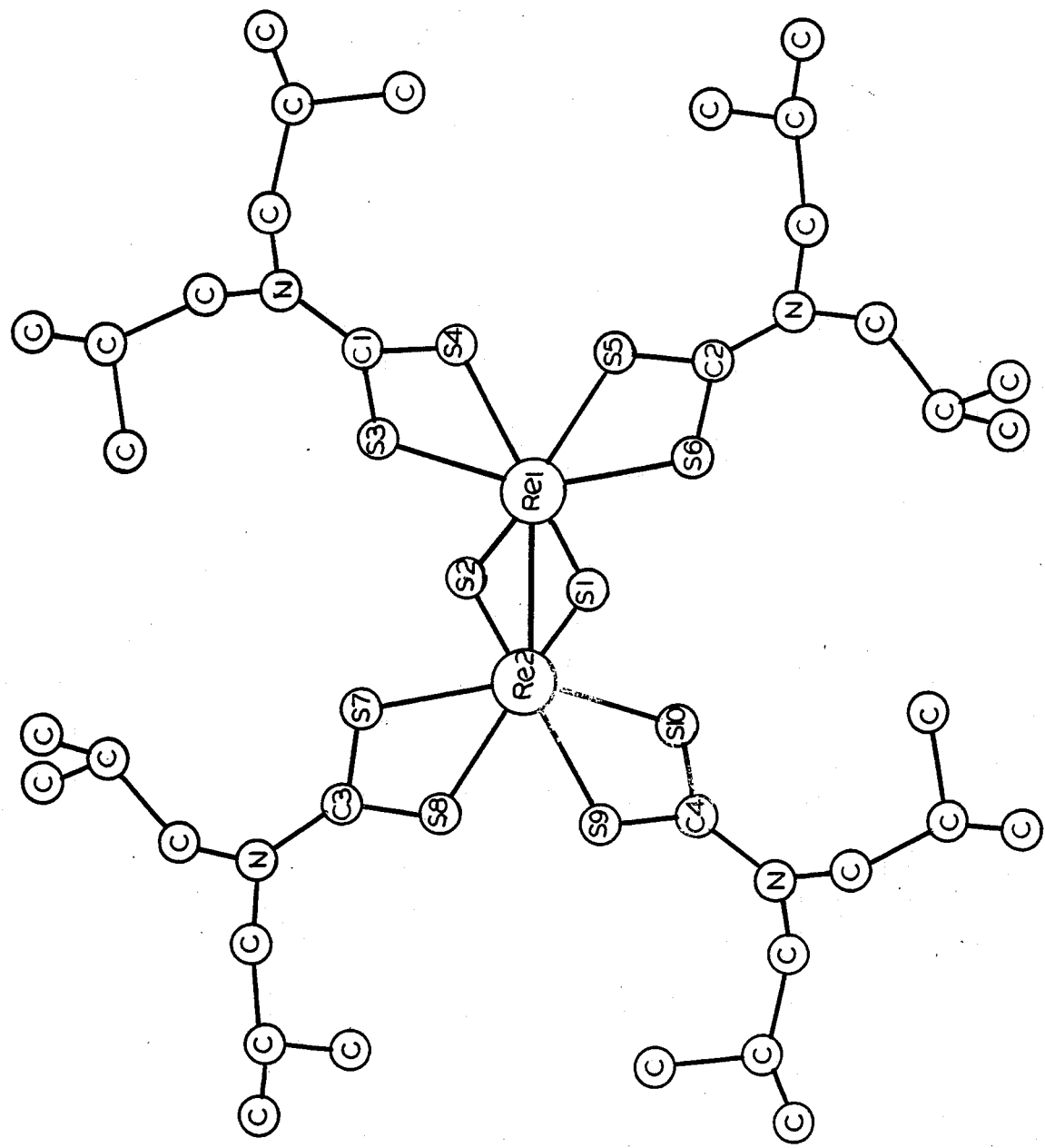

DITHIOACID RHENIUM SULFIDE DIMER COMPOSITIONS

This is a Rule 60 Continuation of U.S. Ser. No. 202,341 filed Jun. 6, 1988, now abandoned, which is based on P.M. 88-CL-002.

FIELD OF THE INVENTION

This invention relates to novel neutral dimeric rhenium dithioacid complexes and their method of preparation.

BACKGROUND OF THE INVENTION

Various rhenium dithiocarbamate complexes have been reported in the literature. (See, for example, Rowbottom et al., *J. Chem. Soc. Dalton*, 1972, pp. 826–830; Rowbottom et al., *J. Chem. Soc. Dalton*, 1974, pp. 684–689; Fletcher et al., *J. Chem. Soc. Dalton*, 1974, pp. 486–489; Gorden et al., *Inorg. Chem.*, 1983, 22, pp. 157–167, and Colton et al., *J. Chem. Soc.*, 1960, pp. 5275–5276.

None of these references disclose a rhenium dithioacid complex containing bridging sulfido ligands in a core similar to that which constitutes an essential feature of this invention.

SUMMARY OF THE INVENTION

Briefly stated, the present invention encompasses a new class of rhenium dithioacid complexes and their method of preparation. The complexes have the general formula $[L_2Re(\mu\text{-}S)]_2$ wherein L is a dithioacid or similar ligand, and $\mu$ denotes the fact that the sulfur atoms in the core of the complex bridge the two rhenium atoms in the complex. Thus, the core structure for such typical compounds is generally of the form:

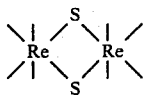

where the dangling valences represent coordination by the ligands, L.

The compositions are made by reacting tetrathioperrhenate salts such as tetraalkyl ammonium tetrathioperrhenate, with a disulfide which upon reduction gives a 1,1-dithiolate ligand.

The compositions are useful as catalysts and catalyst precursors used, for example, in the catalytic dehydropolymerization of tetrahydroquinoline.

BRIEF DESCRIPTION OF THE DRAWING

The sole FIGURE is a depiction of the molecular structure, with the hydrogen atoms omitted, of a complex according to the invention in which the ligand L is diethyldithiocarbamate. In the FIGURE a labeling scheme is included to designate relative positions of certain individual atoms.

DETAILED DESCRIPTION OF THE INVENTION

The neutral dimeric rhenium dithioacid complexes of the present invention may be represented by the formula $[L_2Re(\mu\text{-}S)]_2$ wherein L is 1,1-dithioacid ligand which may be a dithiocarbamate, xanthate, dithiophosphate, dithiophosphinate, or other similar ligand, and wherein $\mu$ denotes the fact that the sulfur atoms in the core of the complex bridge the two rhenium atoms. The preferred ligand is a dithiocarbamate $(S_2CNR_2)$ wherein R is independently a hydrogen or $C_1\text{-}C_{24}$ branched, linear or cycloalkyl group, e.g. preferably methyl, ethyl, n-propyl isopropyl, butyl, isobutyl, t-butyl, or the like; a $C_6\text{-}C_{24}$ aryl, alkyl aryl or aralkyl group or wherein $NR_2$ is a morpholino group. The ligands preferably are all of the same type; however, such is not absolutely necessary.

The compounds of the present invention can be represented by the following general structure:

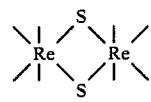

wherein the dangling valences are associated with a ligand L, as defined above.

As indicated, the preferred ligand L is a dithiocarbamate, and in such instance the dimer will have the following structure:

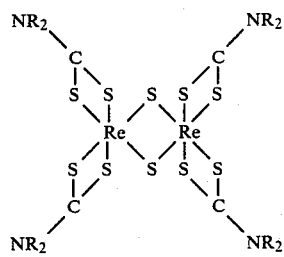

These compositions may be made by reacting a tetrathioperrhenate salt, $MReS_4$, with a disulfide which upon reduction gives a 1,1-dithiolate ligand. Preferably, the cation M in the salt $MReS_4$ is selected from quaternary ammonium, phosphonium and arsonium groups, and especially tetralkyl ammonium groups. Examples of such cations include tetraethyl ammonium, tetraphenyl phosphonium ion, tetraphenyl arsonium ion and the like.

The preparation of tetrathioperrhenate salts is known; however, in copending application Ser. No. 202,342 filed Jun. 6, 1988 an improved method for preparing particularly useful tetrathioperrhenate salts is described. Consequently, such preparation is incorporated herein by reference.

In general, it is preferred to carry out the reaction of the tetrathioperrhenate salt with the disulfide of the appropriate ligand in a solution of an organic solvent. Typical solvents include acetonitrile, dichloromethane, tetrahydrofuran and toluene. Acetonitrile is particularly preferred. Basically, the reactants are mixed for a time sufficient for the formation of the complex. Indeed, the extent of reaction can be visually estimated by noting the amount of solid precipitated from the solution.

In general, the reaction can be conducted at room temperature and pressure. Preferably, the reaction is carried out under inert atmosphere, although this is not required.

The following examples illustrate the present invention.

EXAMPLES

EXAMPLE 1

Tetraethylammonium tetrathioperrhenate (0.25 g, 0.56 mmole) and tetraethylthiuramdisulfide (0.417 g, 1.41 mmole) were dissolved in 30 ml of deaerated acetonitrile. The resulting deep violet solution was stirred under inert atmosphere at room temperature for 18 hours, at which point a green precipitate was separated by filtration, washed with diethylether, and air dried to yield 0.325 g product. The product was characterized by infrared and electronic spectroscopy and single crystal X-ray diffraction analysis. The IR spectral analysis show absorbances in the range of 600, to 250 $cm^{-1}$ which are characteristic of bridging sulfido ligands and $R_2NCS_2^-$ ligands bound to rhenium.

The single crystal X-ray diffraction analysis was carried out as follows:

Single crystals of $[(C_2H_5)_2NHS_2]_4Re_2(\mu\text{-}S)_2$ suitable for X-ray diffraction analysis were grown by diffusion of diethylether into a dichloromethane solution of the complex. One crystal was selected and mounted on a computer-controlled Nicolet Autodiffractometer equipped with graphite monochromatized $MoK_\alpha$ ($\lambda = 0.71073$ Å) radiation source. The crystal was found to be monoclinic, space group $P2_1/c$, with lattice constants $a = 11.084(2)$, $b = 13.815(3)$, $c = 19.945(4)$ Å, $\beta = 92.23(2)°$. Cell volume is $3052(2)$ Å$^3$, $Z = 2$, and the density is 1.522 gm/cm$^{-3}$. A total of 5571 reflections were recorded, and the structure determined from the intensities of these reflections following known procedures.

As illustrated in the Figure, a molecule of $Re_2(\mu\text{-}S)_2[(C_2H_5)_2NCS_2]_4$ contains 2 Re atoms bridged by 2 $S^{2-}$ ligands. A crystallographic inversion center lies midway between the 2 Re atoms in the crystal studied. Each Re is also coordinated by 2 dithiocarbamate ligands, such that the Re atom is bound to a total of 6 S atoms (4 from the 2 dithiocarbamates, and 2 from the bridging sulfides). Selected bond lengths and angles characteristic of the rhenium dimer are given in Table I:

TABLE I

| Bond | Length (Å) | Bond | Angle (°) |
| --- | --- | --- | --- |
| $Re_1\text{-}Re_2$ | 2.546(1) | $Re_1\text{-}S_1\text{-}Re_2$ | 68.1(1) |
| $Re_1\text{-}S_1$ | 2.275(3) | $S_5\text{-}Re_1\text{-}S_6$ | 70.6(1) |
| $Re_1\text{-}S_5$ | 2.511(3) | $S_1\text{-}Re_1\text{-}S_2$ | 111.9(1) |
| $Re_1\text{-}S_6$ | 2.430(3) | $S_{10}\text{-}Re_2\text{-}S_9$ | 70.5(1) |

EXAMPLES 2, 3, 4, and 5

In these examples, the procedure of Example 1 was followed except that R in the dithioacid $((R_2NCS_2)_2)$ used was either methyl, isopropyl, or butyl rather than ethyl as in Example 1. In one instance the dithioacid was morpholino. IR spectral data for the products (including the diethyl dithiocarbamate complex of Example 1) are tabulated in the table which follows:

TABLE 2

| Example | Dithiocarbamate | Wave Number (cm$^{-1}$) |
| --- | --- | --- |
| 1 | Dimethyl dithiocarbamate | 2920(W)*, 1520(S), 1385(S), 1385(S), 1250(M), 1040(S), 980(M), 460(W), 420(M) 355(W) |
| 2 | Diethyl dithiocarbamate | 2960(M), 2920(M), 1495(S), 1460(M), 1430(S), 1355(M), 1270(S), 1210(M), 1150(S), 1070(M), 1000(M), 920(M) 850(M), 780(M), 605(W), 570(W), 425(M), 355(W) |
| 3 | Diisopropyldithiocarbamate | 2960(M), 1480(S), 1450(M), 1440(M), 1365(M), 1325(S), 1190(M), 1140(S), 1040(M), 750(W), 800(W), 850(M), 420(M), 370(W) |
| 4 | Diisobutyldithiocarbamate | 2960(S), 2920(M), 2860(M), 1485(S), 1460(M), 1420(S), 1385(M), 1350(M), 1335(M), 1245(S), 1200(M), 1150(S), 980(W), 940(W), 880(W), 820(W), 625(W), 440(M) 350(W) |
| 5 | 1-morpholine dithiocarbamate | 2960(W), 2900(W), 2860(W), 1490(S), 1430(S), 1300(W), 1270(M), 1230(S), 1120(S) 1025(S), 1000(M), 885(M), 830(W), 670(W), 545(M), 430(M), 530(W) |

It should be understood that the foregoing disclosure, description and examples are only illustrative of the invention. Various changes in the details of the invention would be apparent to the skilled artisan, and may be made within the scope of the appended claims without departing from the spirit of the invention.

What is claimed is:

1. A compound having the formula $[L_2Re\ (\mu\text{-}S)]_2$ wherein L is a 1,1-dithioacid and $\mu$ denotes that the sulphur atoms in the core of the compound bridge the rhenium atoms in the compound.

2. The compound of claim 1 wherein L is selected from dithiocarbamates, xanthates, dithiophosphates, dithiophosphinates and mixtures thereof.

3. The compound of claim 2 wherein L is a dithiocarbamate of the formula $S_2CNR_2$ and R is independently H, a $C_1$ to $C_{24}$ alkyl or cycloalkyl group, a $C_6$ to $C_{24}$ aryl, alkyl aryl or aralkyl group, or $NR_2$ is a morpholino group.

4. The compound of claim 3 wherein R is an alkyl group.

5. A method preparing a compound of the formula $[L_2Re\ (\mu\text{-}S)]_2$ wherein L is a 1,1-dithioacid and $\mu$ signifies that the sulphur atoms in the core of the compound bridge the rhenium atoms therein, comprising: mixing a non-aqueous solution of a tetrathioperrhenate salt with a disulfide of the 1,1-dithioacid, said mixing being for a time sufficient to form the compound.

6. The method of claim 5 wherein said mixing is conducted at ambient temperature.

7. The method of claim 6 wherein said non-aqueous solution is an acetonitrile solution.

8. The method of claim 7 wherein said disulfide is of a 1,1-dithioacid selected from dithiocarbamates, xanthates, dithiophosphates, dithiophosphinates and mixtures thereof.

* * * * *